US006517750B2

(12) United States Patent
Benz et al.

(10) Patent No.: US 6,517,750 B2
(45) Date of Patent: Feb. 11, 2003

(54) METHOD OF FORMING AN INTRAOCULAR LENS

(75) Inventors: Patrick H. Benz, Sarasota, FL (US); Jose A. Ors, Sarasota, FL (US)

(73) Assignee: Benz Research and Development Corporation, Sarasota, FL (US)

(*) Notice: Subject to any disclaimer, the term of this patent is extended or adjusted under 35 U.S.C. 154(b) by 52 days.

(21) Appl. No.: 09/874,015

(22) Filed: Jun. 6, 2001

(65) Prior Publication Data

US 2002/0027302 A1 Mar. 7, 2002

Related U.S. Application Data

(63) Continuation of application No. 09/070,771, filed on May 1, 1998, now Pat. No. 6,267,784.

(51) Int. Cl.[7] .............................. B29D 11/00
(52) U.S. Cl. .................. 264/2.7; 623/6.59; 623/901; 264/1.32; 523/108
(58) Field of Search ............... 623/6.59, 6.4, 623/6.56, 5.15, 5.16, 926, 901; 523/108; 526/329.6; 351/160 H; 264/1.32, 2.6, 2.7

(56) References Cited

U.S. PATENT DOCUMENTS

| 4,379,864 A | 4/1983 | Gallop et al. |
| 4,388,448 A | 6/1983 | Melby |
| 4,582,884 A | 4/1986 | Ratkowski |
| 4,718,906 A | 1/1988 | Mackool |
| 4,764,169 A | 8/1988 | Grendahl |
| 4,769,431 A | 9/1988 | Ratkowski |
| 4,866,148 A | 9/1989 | Geyer et al. |
| 5,147,902 A | 9/1992 | Ichikawa et al. |
| 5,217,491 A | 6/1993 | Vanderbilt |
| 5,326,506 A | 7/1994 | Vanderbilt |
| 5,330,911 A | 7/1994 | Hubbell et al. |
| 5,480,950 A | 1/1996 | Wang et al. |
| 5,532,289 A | 7/1996 | Benz et al. |
| 6,267,784 B1 * | 7/2001 | Benz et al. ............ 623/6.59 |

FOREIGN PATENT DOCUMENTS

| EP | 0 485 197 | 5/1992 |
| GB | 2196973 | 5/1988 |
| WO | WO 90 09230 | 8/1990 |

OTHER PUBLICATIONS

Abstract; J. Cataract Refract Surg—vol. 17, Mar. 1991 "Cytotoxic effects of residual chemicals from polymeric biomaterials for artificial soft intraocular issues".

Businger, die Kontakinsen 7–8, 4 (1997).

Benz et al., Contact Lens Spectrum, Jul. 1997, pp. 40–46.

Clinical Studies by Businger in Contact Lens Spectru, Aug. 1995, pp. 19–25.

Pescossolido et al., Contactologia, 15D, 64–7 (1993).

Benz Technical Manual, Apr. 1993.

Benz Technical Manual, Sep. 1992.

Ors et al., Proceedings of ACS Division of PMSE 56, 744 (1987).

Kloosterboer et al., Phillips Tech. Rev. 40, 928 (1982).

(List continued on next page.)

*Primary Examiner*—Paul B. Prebilic
(74) *Attorney, Agent, or Firm*—Foley & Lardner

(57) ABSTRACT

A method of making a one-piece intraocular lens formed from a copolymer of a hydrophilic monomer and an alkoxyalkylmethacrylate. The intraocular lens is foldable so as to be insertable through a small incision in the eye. Copolymers of the lens have an equilibrium water content of from about 10 to about 38 percent by weight based on the total weight of the hydrated copolymer.

27 Claims, 2 Drawing Sheets

OTHER PUBLICATIONS

Macret et al., "Hydroxyalkyl methacrylates: hydrogel formation based on the radical copolymerization of 2–hydroxyalkyl–methacrylate and 2,3–dihydroxypropyl–methacrylate" *Polymers* 23:748–753 (1982).

Macret et al., "Hydroxyalkyl methacrylates: Kinetic investigations of radical polymerizations of pure 2–hydroxyethyl methacrylate and 2,3–dihydroxypropyl methacrylate and the radical copolymerization of their mixtures" *Polymer* 23:81–90 (1982).

Yasuda et al., "Hydrogels of Poly(hydroxyethyl Methacrylate) and Hydroxyethyl Methacrylate–Glycerol Monomethacrylate Copolymers" *Journal of Pol. Sci. Part A–1* 4:2913–2927 (1966).

Refojo, "Hydrogels from 2–Hydroxyethyl Methacrylate and Propylene Glycol Monoacrylate" *Journal of App. Pol. Sci.* 9:2425–2434 (1965).

* cited by examiner

METHOD OF FORMING AN INTRAOCULAR LENS

BACKGROUND OF THE INVENTION

This application is a continuation of U.S. Ser. No. 09/070,771 filed May 1, 1998, now U.S. Pat. No. 6,267,784.

1. Field of the Invention

This invention relates to intraocular lenses. The invention also relates to methods of making such lenses, and to copolymers useful, for example, in intraocular lenses.

2. Description of Related Art

Various types of intraocular lenses (IOLs) are known. For example, there are known one-piece IOLs and composite IOL having multiple pieces. A one-piece IOL is one where both optic and non-optic portions are made from one material. The non-optic portions are referred to as haptic portions, and are used for attachment purposes. Two general designs for the haptics are a "plate-type" and a "C-haptic" type, both of which have a variety of shapes. A plate design is shown in FIGS. 1A and 1B. A "C" design is shown in FIGS. 2A and 2B. These Figures are discussed in more detail below.

It is desired to reduce the length of incision needed to insert the IOL into the eye. Reducing the length of the incision requires the use of a very soft material for the lens; soft enough to permit the lens to be folded, inserted through the incision, and released. Thus, intraocular lenses are preferably foldable so that they can be easily inserted into the eye. Approaches to achieve foldable materials include use of lenses formed of hydrophobic silicone-polymers, certain hydrophilic 2-HEMA homopolymers, and composites of a hydrophilic optical core with hydrophobic poly(methyl)methacrylate (p-MMA) based haptics.

IOLs with mechanically-attached haptics are lenses where the optic-portion and the haptic-portion are made separately, usually from different materials, and attached. For example, the lens portion can be made of a hydrogel or silicone-based material and the C-shape haptics from a rigid material like p-MMA. The p-MMA haptics are attached to holes drilled into the optic portion.

Although P-MMA is the traditional hydrophobic IOL it is not easily foldable and requires a relatively large incision for insertion. To make hydrophobic materials foldable, there has been included rubber-like materials, such as silicone derivatives, into the rigid polymer matrix or use of materials consisting primarily of silicone derivatives. Although the softness of a primarily silicone material is ideal for folding prior to insertion, when the lens and its haptics unfold in the eye, the almost gel-like softness of the lens makes it difficult for a surgeon to properly position the lens in the eye. Furthermore, the silicone lens often does not provide sufficient rigidity for the lens after insertion and the combination of deformation from compressive forces along with lens movement can produce lens distortion and compromise the optical integrity of the lens.

Because of its inherent properties, p-hydroxyethyl methacrylate (a homopolymer of HEMA) has been used as a foldable material for IOLs. However, the low refractive index of p-HEMA when hydrated leads to limitations in the optical center design and a compromise between its folding ability and its optical requirements.

One of the limitations of one-piece P-HEMA hydrogel lenses has been that the haptic portion lacks the desired dimensional stability and can compromise lens positioning. To address this issue, polymer materials have been combined to give a soft, foldable intraocular composite lens such as P-HEMA or other soft acrylic material for the optic zone, and a rigid structure around the outside of the lens, made from a hard plastic such as P-MMA. See U.S. Pat. No. 4,718,906 and U.S. Pat. No. 5,326,506, both hereby incorporated by reference in their entireties, which describe composite IOLs. These multicomponent materials are made by embedding one material in the other, or by concurrent extrusion processes, or by solidifying the hard material about the soft material, or by forming an interpenetrating network of the rigid component into a preformed hydrophilic core.

U.S. Pat. No. 5,326,506, discloses a composite intraocular lens including a soft, pliable inner lens optic using rigid haptics. The lens optic material is a low water content material such as a copolymer of 2-HEMA and hydroxy hexylmethacrylate which has a high refractive index due to its low water content. The hard yet foldable P-MMA haptics, are formed by an interpenetrating network.

An article by Chirila et al., J. Cataract Refract. Surf., pp. 154–162, Vol. 17, March 1991 discusses the toxicity effects of residual monomers, such as 2-hydroxyethyl methacrylate, methyl methacrylate, and 2-ethoxyethyl methacrylate, in IOLs. One piece IOLs are not proposed.

U.S. Pat. No. 4,764,169, hereby incorporated by reference in its entirety, discloses a composite intraocular lens including a small, hard inner lens optic and a soft, pliable skirt surrounding the lens optic. The lens optic material is a relatively hard material such as P-MMA, polysulfone, or polycarbonate. The soft, pliable skirt is a silicone, hydrogel or like material.

SUMMARY OF THE INVENTION

It is an object of the present invention to provide a one-piece IOL that overcomes the disadvantages of known one-piece IOLs and composite IOLs.

It is an object of the invention to provide an intraocular lens that is foldable so as to be insertable through a small incision in the eye.

It is also an object of the present invention to provide a one-piece, intraocular lens having a soft, foldable optic portion and haptic portion, wherein the optic and haptic portions are made from the same soft hydrogel material, that protects the eye tissue at the point of contact without sacrificing the lens positioning properties.

It is also an object of the invention to provide a one-piece intraocular lens having a soft, foldable optic portion and haptic portion that has excellent biocompatibility with the patient's eye.

It is also an object of the invention to provide a material useful in both the optic and haptic portions of the IOL.

In accordance with these and other objectives there has been provided in accordance with the present invention a one-piece intraocular lens formed from a copolymer of a hydrophilic monomer and an alkoxyalkyl methacrylate.

In accordance with these objectives, there is also provided a one-piece intraocular lens, wherein both the optic and haptic portions are formed from a copolymer of a monomer of formula HO-$R_1$-MA and a monomer of formula $R_2$-O-$R_3$-MA, wherein $R_1$, $R_2$, and $R_3$ are independently selected from alkyl groups having 1 to 6 carbon atoms, and where MA is methacrylate.

In accordance with the invention, there is also provided an intraocular lens including a haptic portion and an optic portion, wherein the haptic and optic portion are formed of the same or different copolymer of a hydrophilic monomer and an alkoxyalkyl methacrylate.

In accordance with the invention, there is also provided a hydrogel copolymer of a hydrophilic monomer and an alkoxyalkyl methacrylate, wherein the hydrophilic monomer is of formula HO—$R_1$—MA and the alkoxyalkyl methacrylate is of formula $R_2$—O—$R_3$—MA, wherein $R_1$, $R_2$, and $R_3$ are independently selected from alkyl groups having 1 to 6 carbon atoms, where MA is methacrylate, and wherein the hydrogel has a water content of from about 10 to about 38 percent by weight, based on the weight of the copolymer.

Further objects, features, and advantages of the present invention will become apparent from the detailed description of preferred embodiments that follows.

DETAILED DESCRIPTION OF PREFERRED EMBODIMENTS

The intraocular lens of the present invention is a one-piece lens having a soft, foldable central optic region and an outer peripheral region (haptic-region). Both regions are made of a copolymer of a hydrophilic monomer and an alkoxyalkyl methacrylate monomer. Generally the optic and haptic are made of the same copolymer. Unlike the composite materials described in the art, wherein the optic and haptic regions are formed of different types of polymers, in the present IOL, the optic and haptic regions are formed of the same kind of copolymer; namely a copolymer of a hydrophilic monomer and an alkoxyalkyl methacrylate. Preferably the optic and haptic regions are formed from the same copolymer.

Both the central optic zone of the IOL and its haptics are manufactured from a copolymer capable of being folded so that the intraocular lens can be inserted through a small incision. The haptic portion of the lens, although made from the same type of copolymer as the optic portion, provides the required support for the lens in the eye after insertion and unfolding of the lens and tends to help stabilize the position of the lens after insertion and the closure of the incision. The haptic portion design can be any desired, for example, either a plate type or graduated thickness spiral filaments, also known as a C-loop design.

Figure 1A:
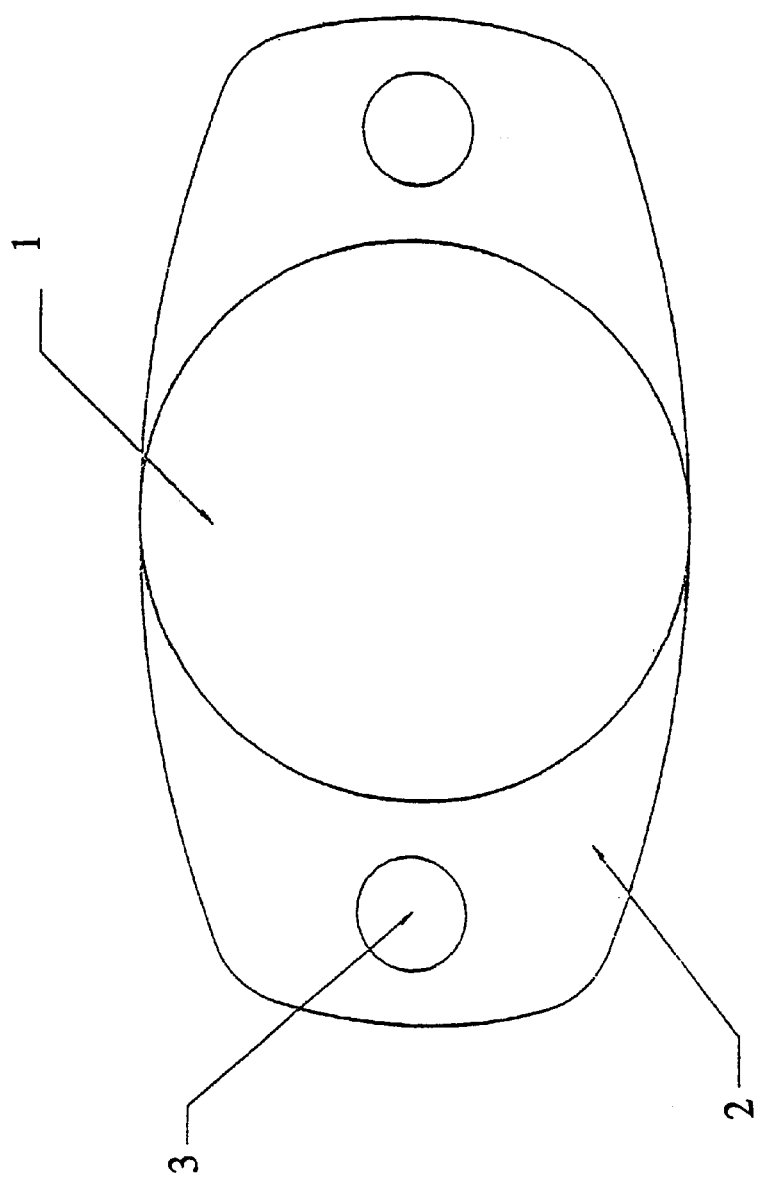
FIG. 1A is a top view of an intraocular lens having a plate-shaped haptic.
Figure 1B:
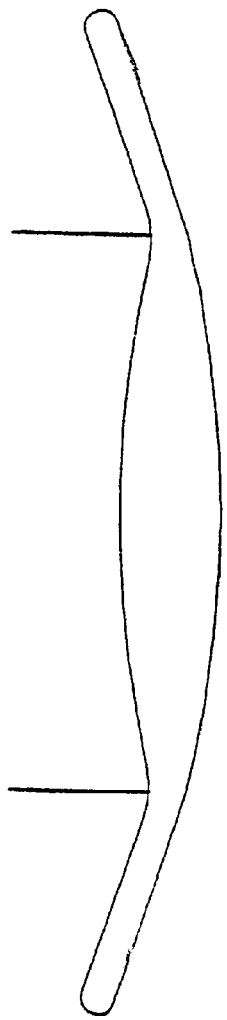
FIG. 1B is a side view of the intraocular lens having a plate-shaped haptic shown in FIG. 1A.
Figure 2A:
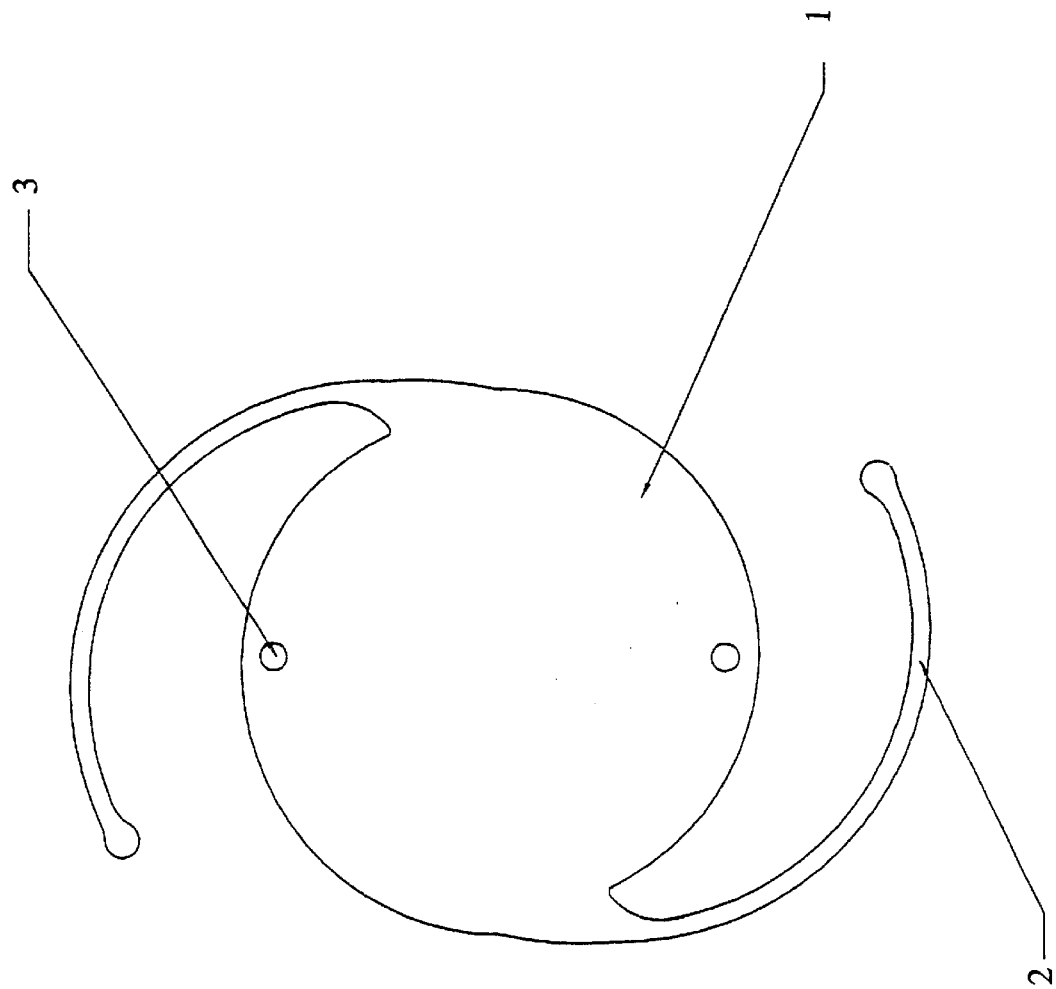
FIG. 2A is a top view of an intraocular lens having a C-shaped haptic.
Figure 2B:
FIG. 2B is a side view of the intraocular lens having a C-shaped haptic shown in FIG. 2A.

FIGS. 1A, 1B, 2A, and 2B illustrate examples of IOLs in accordance with the present invention. The figures are for illustrative purposes only and do not limit the scope of the invention. For instance, the IOL can be any type of IOL, so long as the IOL is a one-piece IOL wherein the optic and haptic portions include the same type of copolymer. In the figures, 1 is the optic portion of the lens, 2 is the haptic portion, and 3 is a positioning hole. One skilled in the art of IOLs understands the functions of these portions of the IOL.

The optic portion 1 can be approximately 6 mm in diameter prior to hydration. The 6 mm diameter is fairly standard in the art, and is generally chosen to cover the pupil in its fully dilated state under naturally occurring conditions. However, other sizes are possible and the present invention is not limited to any particular diameter or size of IOL. Furthermore, it is not necessary that the lens optic portion be circular; it could also be oval, square, or any other shape as is desired.

The intraocular lens comprises one or more non-optical haptic components 2 extending away from the outermost peripheral surface of the optic portion. The haptic components can be of any desired shape, for example, graduated spiral filaments or flat plate sections and are used to support the lens within the posterior chamber of the eye. Lenses having any desired design configuration can be fabricated. Further, although two types of haptic designs are shown in the figures, the haptics can have configurations other than those illustrated. Should the IOL include other components besides the optical and haptic portions, such other portions can be made of a copolymer as are the haptic and optic portions, or if desired, another material.

The IOLs of the invention may be inserted into the eye in known manners. For example, the IOL may be folded prior to insertion into the eye by small, thin forceps of the type typically used by ophthalmic surgeons. After the lens is in the targeted location, it is released to unfold. The IOL of the present invention is made of a physiologically inert soft polymeric material that is capable of providing a clear, transparent, refractive lens body even after folding and unfolding.

The optical and haptic portions of the IOL of the present invention are formed from the same or different, preferably the same, copolymer of a hydrophilic monomer and an alkoxyalkyl methacrylate. The hydrophilic monomer can be selected from any desired hydrophilic monomer known, for example, a monomer of formula HO—$R_1$—MA, wherein $R_1$ is an alkyl group having 1 to 6 carbon atoms, preferably 1 to 4 carbon atoms. The alkoxyalkyl methacrylate can be formed from any such monomers, for example, a monomer of formula $R_2$—O—$R_3$—MA, wherein $R_2$ and $R_3$ are independently selected from alkyl groups having 1 to 6 carbon atoms, preferably 1 to 4 carbon atoms. The copolymer preferably contains at least about 90 weight percent, preferably at least about 95 weight percent based on the total weight of the copolymer, of the total of the hydrophilic monomer(s) and the alkoxy-alkyl methacrylate(s).

The amount of the hydrophilic monomer and the alkoxyalkylmethacrylate monomers in the copolymer, can be varied within a wide range to give the desired characteristics to the IOL. Generally the amount of hydrophilic monomer is about 40 to about 95 percent by weight, preferably about 50 to about 90 percent, more preferably about 60 to about 80 percent based on the total weight of the copolymer. Examples of useful hydrophilic monomers include hydroxyethyl methacrylate (HEMA=HO-$R_1$-MA where $R_1$ is ethyl) and hydroxypropyl methacrylate (HPMA=HO-$R_1$-MA where $R_1$ is propyl).

The alkoxyalkyl methacrylate monomers generally comprise from about 5 to about 60 percent, preferably about 10 to about 50 percent, more preferably about 20 to about 40 percent, of the copolymers. Examples of monomers useful as the alkoxyalkyl methacrylate include ethoxyethyl methacrylate (EOEMA=$R_2$—O—$R_3$—MA where $R_2$ and $R_3$ are ethyl), methoxyethyl methacrylate (MOEMA=$R_2$—O—$R_3$—MA where $R_2$ is methyl and $R_3$ is ethyl), propoxyethyl methacrylate (n-POEMA=$R_2$—O—$R_3$—MA where $R_2$ is propyl and $R_3$ is ethyl), and butoxyethyl methacrylate (n-BuOEMA=$R_2$—O—$R_3$—MA where $R_2$=n-butyl and $R_3$=ethyl).

The copolymers can be prepared using conventional polymerization techniques known to those in the field of polymer chemistry. Crosslinkers can be added during polymerization as known in the art. For example, any crosslinking or difunctional monomer used in the art such as ethylene glycol dimethacrylate (EGDMA), can be used in effective amounts to give the desired crosslinking, for example, in a concentration range of 0 to about 10 percent, such as about 0.01 to about 0.4 percent by weight, based on the weight of the polymer.

Also, if desired an initiator can be used in the polymerization. Any initiator commonly used in the art, such as azo derivatives, like 2,2-azobis (2,4-dimethylvaleronitrile) and propanenitrile,2-methyl,2,2'-azobis, can be used. The initiator is used in an amount effective for initiation purposes, and is generally present from about 0.01 to 1.0% by weight, based on the weight of the copolymer. Thus, the term copolymer for the purposes of this application means that the polymer The copolymer used in the present invention can include in addition to a hydrophilic monomer and an alkoxyalkyl methacrylate, additional monomers, such as additional hydrophilic monomers or acrylates, as well as monomers that impart UV absorption to the copolymer. Any monomer copolymerizable with the hydrophilic monomer and the alkoxyalkyl methacrylate monomers can optionally be used, so long as such does not materially, adversely effect the basic characteristics of the IOL. Examples of useful additional monomers that can used are described in U.S. Pat. No. 5,326,506, hereby incorporated by reference, directed to a composite IOL. In particular, the monomers indicated as copolymerizable with the HEMA in the '506 patent, for the optic portions of the patent's IOL lens, can be used as optional additional monomers in the copolymers of the present invention. Such optional additional monomers, preferably are present in a total amount of not more than 10 weight percent, generally less than 5 weight percent, based on the total weight of the copolymer. Thus, the term copolymer for the purposes of this application means that the polymer is formed from 2 or more different polymerizable monomers.

As mentioned above, it may be useful to add crosslinking agents such as ethylene glycol dimethacrylate (EGDMA), for example, to enhance the resulting copolymer's dimensional stability. It may also be advantageous to add ultraviolet (UV) absorbing compounds with the lens monomers prior to polymerization for incorporation into the resultant polymer, as is known in the art. The UV absorber should preferably be capable of polymerization into the lens matrix so as to resist extraction under physiologic conditions. The UV-absorbing monomer can be present in an amount effective to give the desired UV-absorbing properties, generally less than 4 percent by weight of the copolymer, such as from 0.01 to about 1 percent by weight of the copolymer.

Table 1 below summarizes exemplary constituents useful in making the copolymer for the IOLs of the present invention.

TABLE 1

| HO-R$_1$-MA | Concentration Range | R$_2$-O-R$_3$MA | | Concentration |
|---|---|---|---|---|
| R$_1$ = Ethyl | (Wt. %) | R$_2$ = | R$_3$ = | Range (Wt. %) |
| HEMA | 40 to 95 | Ethyl, Methyl, n-Propyl, i-Propyl, n-Butyl, i-Butyl, or sec-Butyl | Ethyl, or Propyl | 5 to 60 |

TABLE 1-continued

| HO-R$_1$-MA | | R$_2$-O-R$_3$-MA | | |
|---|---|---|---|---|
| R$_1$ = Propyl | | R$_2$ = | R$_3$= | |
| HPMA | 40 to 95 | Ethyl, Methyl, n-Propyl, i-Propyl, n-Butyl, or i-Butyl | Ethyl, or Propyl | 5 to 60 |

Examples of specific copolymers useful in the present invention are shown below in Table 2.

TABLE 2

| | General | R$_2$-O-R$_3$-MA | | General |
|---|---|---|---|---|
| HO-R$_1$-MA | Range | R$_3$ = Ethyl | R$_3$ = Propyl | Range |
| HEMA HPMA | 40 to 95 | EOEMA MeOEMA n-PrOEMA i-PrOEMA n-BuOEMA i-BuOEMA sec-BuOEMA | EOPMA MeOPMA n-PrOPMA i-PrOPMA n-BuOPMA i-BuOPMA sec-BuOPMA | 5 to 60 |

The copolymers used in the IOLs preferably have a refractive index (RI) of greater than about 1.4 generally from about 1.4 to about 1.5. This is significantly greater than the RI of p-HEMA. An advantage of hydrogel copolymers of the present invention is that they can be folded prior to insertion, thereby reducing the size of the incision. Generally, the RI value for a hydrogel decreases progressively with increasing water content. The RI value of a material influences the design and the parameters of an IOL. Hence, besides biocompatibility, an ideal IOL would be foldable, have the ability to quickly regain its shape and optical quality after insertion, and have a high RI value. The IOLs of the present invention have been found to have these desired characteristics. That is, the IOLs of the present invention fulfill the requirements of a high performance intraocular lens and have excellent folding characteristics, relatively high refraction index, and excellent unfolding characteristics.

A preferred material for both the optical and haptic regions of the IOL is a copolymer of 2-hydroxyethyl methacrylate (2-HEMA) and ethoxyethyl methacrylate (EOEMA).

The hydrogels of the copolymers have a low water content, generally from about 10 to about 38 percent, preferably about 18 to 32 percent by weight, based on the total weight of the copolymer.

The IOLs of the present invention may be formed by methods known in the art. For example, in an exemplary process first the monomers that form the copolymer are polymerized into a polymer rod; polymer blanks or discs are formed from the rod, and then the blanks are cut, for example, by a lathe into the intraocular lens. The rods can be made by a procedure which begins with polymerizing in a tubular or cylindrical mold a liquid mixture of initiator and co-monomers such as 2-HEMA and EOEMA, to form an optically clear soft lens body. As discussed above, it may be desirable to incorporate cross-linking materials and ultraviolet-absorbing compounds during polymerization or into the resultant polymer matrix. The polymer rods are then cut and centerless ground, into blanks of the desired diameter and thickness by lathe cutting and machine milled in the conventional manner into an intraocular lens.

Generally, the composite material rod is lathe cut or ground to a diameter 0.5 to 2.0 mm thicker than the required distance from the center of the lens body to the furthest edge of the legs or haptics. This rod is then sawed or otherwise cut into blanks of uniform thickness. The blanks are then heat treated and ground and lapped to a diameter and thickness suitable for lathe cutting and machine milling in the conventional manner into the intraocular lens of the present invention.

A general description of a stepwise process for forming the blanks into IOLs is set forth in the flow chart below. One having ordinary skill in the field of IOL manufacturing, from a review of the present specification, can make IOLs using the general knowledge in the art on IOL manufacture.

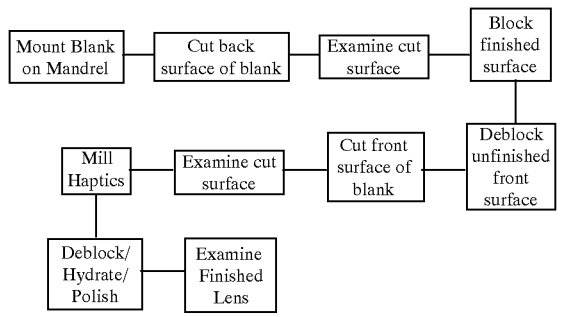

The invention also relates to a hydrogel copolymer of a hydrophilic monomer and an alkoxyalkyl methacrylate, wherein the hydrophilic monomer is of formula HO—$R_1$—MA and the alkoxyalkyl methacrylate is of formula $R_2$—O—$R_3$—MA, wherein $R_1$, $R_2$, and $R_3$ are independently selected from alkyl groups having 1 to 6 carbon atoms, wherein the hydrogel has a water content of from about 10 to about 38 percent by weight, based on the weight of the copolymer. The hydrophilic and alkoxyalkyl methacrylate monomers can be selected from those mentioned above, and the copolymer can include the proportion of monomers and optional other monomers discussed above. The copolymer can be formed as discussed above.

These copolymers can be used in numerous applications, such as in contact lenses, as the optical portion of IOLs, as the haptic portion of an IOL, and as discussed above, as both the optical and haptic portion of the IOL.

The invention is illustrated by the following examples. The examples only illustrate the invention, and do not limit it.

EXAMPLE I

Preparation of HEMA/EOEMA Copolymer with 18% Water Content 548.3 grams of 2-HEMA were mixed with 446.1 grams of EOEMA and 0.7 grams of 2,2-azobis (2,4-dimethylvaleronitrile) were added. The total diester concentration was adjusted to 0.3% by weight with ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The polymer was then removed from the molds and formed into contact lens blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground and lapped to right cylinder with the desired dimensions.

EXAMPLE II

Preparation of HEMA/EOEMA Copolymer with 25% Water Content 707.8 grams of 2-HEMA were mixed with 287.0 grams of EOEMA and 0.7 grams of 2,2-azobis (2,4-dimethylvaleronitrile) were added. The total diester concentration was adjusted to 0.3% by eight with ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The polymer was then removed from the molds and formed into contact lens blanks. The mechanical formation process comprised cutting the polymer into cylinders of 0.5 to 0.65 inches (1.27 to 1.65 cm.) in diameter and 0.1 to 0.2 inches (0.25 to 0.51 cm.) in thickness). The blanks were further cured at 100° C. for 5 hours. After curing, the blanks were ground and lapped to right cylinder with the desired dimensions.

EXAMPLE III

Preparation of HEMA/EOEMA Copolymer with 24% Water Content and UV-Protection 1770.4 grams of 2-HEMA were mixed with 717.6 grams of EOEMA, 12.5 grams of methacryloxy siloxane-2-hydroxy benzophenone and 1.75 grams of 2,2-azobis (2,4-dimethylvaleronitrile) were added. The total diester concentration was adjusted to 0.25% by weight with ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The polymer was then removed from the molds and formed into contact lens blanks. The mechanical formation process included cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground and lapped to right cylinder with the desired dimensions.

EXAMPLE IV

Preparation of HEMA/EOEMA Copolymer with 28% Water Content 763.1 grams of 2-HEMA were mixed with 231.9 grams of EOEMA and 0.7 grams of 2,2-azobis (2,4-dimethylvaleronitrile) were added. The total diester concentration was adjusted to 0.3% by eight with ethylene glycol dimethacrylate (EGDMA). The mixture was degassed while applying vigorous stirring. The mixture was dispensed into cylindrical molds, polymerized at 30° C. for 10 hours, and post-cured at 100° C. for 5 hours. The polymer was then removed from the molds and formed into contact lens blanks. The mechanical formation process comprises cutting the polymer into cylinders of 0.5 to 0.65 inches (1.27 to 1.65 cm.) in diameter and 0.1 to 0.2 inches (0.25 to 0.51 cm.) in thickness. The blanks were further cured at 100° C. for 5 hours. After curing, the blanks were ground and lapped into right cylinder with the desired dimensions.

The blanks formed in the above examples can be formed into one piece IOLs using conventional techniques well known to those in the art. Preferably, but not necessarily, both the optic and haptic portions are formed of the same copolymer.

The formulations of the Examples are summarized in Table 3 below.

TABLE 3

| Component | EXAMPLE 1 (Wt. in grams) | EXAMPLE 2 (Wt. in grams) | EXAMPLE 3 (Wt. in grams) | EXAMPLE 4 (Wt. in grams) |
|---|---|---|---|---|
| 2-HEMA | 548.2 | 707.8 | 1770.4 | 763.1 |
| EOEMA | 446.1 | 287.0 | 717.6 | 231.9 |
| EGDMA | 2.5 | 2, 5 | 6.3 | 2.5 |
| 2,2-azobis . . . | 0.7 | 0.7 | 1.75 | 0.7 |
| UV-Monomer | — | — | 12.5 | — |

The properties of the example formulations are shown in Table 4 below.

TABLE 4

| PROPERTY | EXAMPLE 1 | EXAMPLE 2 | EXAMPLE 3 | EXAMPLE 4 |
|---|---|---|---|---|
| Water Content (%) | 18 | 25 | 24 | 28 |
| Expansion Coefficient: | not measured | | | not measured |
| Linear | | 1.11 | 1.11 | |
| Radial | | 1.11 | 1.11 | |
| Refractive Index: | | | | not measured |
| Dry | 1.4913 | 1.5011 | 1.495 | |
| Wet | 1.4704 | 1.4597 | 1.4614 | |
| Hardness (Shore D) | 81 | 86 | 86 | not measured |

(1) Water content and residuals are determined using a gravimetric method that records the wet and dry weights of a number of sample discs through 2 hydration and drying cycles.
(2) Expansion coefficients (radial and linear) are determined by using fabrication lenses of a design that yields even thickness lenses. Both linear and radial dimensions of the lens are measured in the dry state, followed by lens hydration and repeat of the linear and radial dimension measurements. The coefficients are obtain from the ratios of wet and dry.
(3) Refractive Index is obtained on both dry and hydrated buttons using an Abbe 3L Refractometer calibrated with 1-bromonaphthalene.
(4) Shore D Hardness is obtained using a Shore D durometer (Serial No. 9075) with a calibrated reference block D34.

While several embodiments of the invention have been described, it will be understood that it is capable of further modifications, and this application is intended to cover any variations, uses, or adaptations of the invention, following in general the principles of the invention and including such departures from the present disclosure as to come within knowledge or customary practice in the art to which the invention pertains, and as may be applied to the essential features hereinbefore set forth and falling within the scope of the invention or the limits of the appended claims.

What is claimed is:

1. A method of forming a one-piece intraocular lens, comprising:
    (a) polymerizing a mixture comprising a hydrophilic monomer, an alkoxyalkyl methacrylate monomer, and a crosslinking monomer to form a copolymer comprising an incorporated hydrophilic monomer, an incorporated alkoxyalkyl methacrylate monomer, and at least 0.25 percent up to about 10 percent by weight of an incorporated crosslinking monomer based on the total weight of the dry copolymer;
    (b) forming the copolymer into the one-piece intraocular lens, wherein the one-piece intraocular lens comprises a haptic portion and an optic portion formed from the copolymer and the hydrated copolymer has an equilibrium water content of from 38 percent to about 10 percent by weight based on the total weight of the hydrated copolymer.

2. The method of forming a one-piece intraocular lens according to claim 1, wherein the hydrophilic monomer comprises a monomer of the formula $HO-R_1-MA$ and the alkoxyalkyl methacrylate monomer comprises a monomer of the formula $R_2-O-R_3-MA$, wherein $R_1$, $R_2$, and $R_3$ are independently selected from alkyl groups having 1 to 6 carbon atoms and MA is methacrylate.

3. The method of forming a one-piece intraocular lens according to claim 2, wherein the copolymer consists essentially of incorporated monomers of the formula $R_2-O-R_3-MA$ and the formula $HO-R_1-MA$, and the incorporated crosslinking monomer.

4. The method of forming a one-piece intraocular lens according to claim 2, wherein $R_1$, $R_2$, and $R_3$ are independently selected from alkyl groups having 1 to 4 carbon atoms.

5. The method of forming a one-piece intraocular lens according to claim 1, wherein the one-piece intraocular lens is foldable.

6. The method of forming a one-piece intraocular lens according to claim 1, wherein the copolymer has a refractive index of greater than about 1.4.

7. The method of forming a one-piece intraocular lens according to claim 1, wherein the hydrophilic monomer comprises hydroxyethyl methacrylate or hydroxypropyl methacrylate.

8. The method of forming a one-piece intraocular lens according to claim 1, wherein the alkoxyalkyl methacrylate monomer comprises one or more monomer selected from the group consisting of ethoxyethyl methacrylate, methoxyethyl methacrylate, propoxyethyl methacrylate, and butoxyethyl methacrylate.

9. The method of forming a one-piece intraocular lens according to claim 1, wherein the copolymer comprises about 40 to about 95 percent by weight based on the total weight of the dry copolymer of the hydrophilic monomer, and about 5 to about 60 percent by weight of the alkoxyalkyl methacrylate monomer, based on the total weight of the dry copolymer.

10. The method of forming a one-piece intraocular lens according to claim 1, wherein the copolymer comprises about 50 to about 80 percent by weight based on the total weight of the dry copolymer of the hydrophilic monomer and about 20 to about 50 percent by weight of the alkoxyalkyl methacrylate monomer, based on the total weight of the dry copolymer.

11. The method of forming a one-piece intraocular lens according to claim 1, wherein the crosslinking monomer is ethylene glycol dimethacrylate.

12. The method of forming a one-piece intraocular lens according to claim 1, wherein the mixture comprising the hydrophilic monomer, the alkoxyalkyl methacrylate monomer, and the crosslinking monomer further comprises a UV-monomer.

13. The method of forming a one-piece intraocular lens according to claim 1, further comprising (c) hydrating the copolymer to form a hydrated copolymer.

14. The method of forming a one-piece intraocular lens according to claim 1, wherein the hydrated copolymer has an equilibrium water content of from 18 to 32 percent by weight based on the total weight of the hydrated copolymer.

15. The method of forming a one-piece intraocular lens according to claim 1, wherein the total weight of the hydrophilic and the alkoxyalkyl methacrylate monomer in the copolymer is at least 90 percent by weight based on the total weight of the dry copolymer.

16. The method of forming a one-piece intraocular lens according to claim 1, wherein the total weight of the hydrophilic monomer and the alkoxyalkyl methacrylate monomer in the copolymer is at least 95 percent by weight based on the total weight of the dry copolymer.

17. The method of forming a one-piece intraocular lens according to claim 1, wherein the mixture comprising the hydrophilic monomer, the alkoxyalkyl methacrylate monomer, and the crosslinking monomer further comprises a polymerization initiator.

18. The method of forming a one-piece intraocular lens according to claim 1, wherein the mixture comprising the hydrophilic monomer, the alkoxyalkyl methacrylate monomer, and the crosslinking monomer is polymerized in a tubular or cylindrical mold.

19. The method of forming a one-piece intraocular lens according to claim 1, wherein the mixture comprising the hydrophilic monomer, the alkoxyalkyl methacrylate monomer, and the crosslinking monomer is polymerized into a polymer rod comprising the copolymer.

20. The method of forming a one-piece intraocular lens according to claim 19, wherein the method further comprises forming a polymer blank or a polymer disc from the polymer rod and forming the intraocular lens from the polymer blank or the polymer disc.

21. A method of forming a one-piece intraocular lens, comprising:
  (a) polymerizing a mixture comprising a hydrophilic monomer, an alkoxyalkyl methacrylate monomer, and a crosslinking monomer to form a copolymer comprising an incorporated hydrophilic monomer, an incorporated alkoxyalkyl methacrylate monomer, and an incorporated crosslinking monomer;
  (b) forming the copolymer into the one-piece intraocular lens, wherein the one-piece intraocular lens comprises a haptic portion and an optic portion formed from the copolymer, and further wherein the copolymer comprises about 40 to about 95 percent by weight of the hydrophilic monomer based on the total weight of the dry copolymer, about 5 to about 60 percent by weight of the alkoxyalkyl methacrylate monomer based on the total weight of the dry copolymer, and at least 0.25 percent up to about 10 percent of the crosslinking monomer based on the total weight of the dry copolymer.

22. The method of forming a one-piece intraocular lens according to claim 21, wherein the hydrophilic monomer is of the formula $HO-R_1-MA$ and the alkoxyalkyl methacrylate monomer is of the formula $R_2-O-R_3-MA$, wherein $R_1$, $R_2$, and $R_3$ are independently selected from alkyl groups having 1 to 6 carbon atoms, and MA is methacrylate.

23. The method of forming a one-piece intraocular lens according to claim 21, wherein the crosslinking monomer is ethylene glycol dimethacrylate.

24. The method of forming a one-piece intraocular lens according to claim 21, wherein the mixture comprising the hydrophilic monomer, the alkoxyalkyl methacrylate monomer, and the crosslinking monomer further comprises a polymerization initiator.

25. The method of forming a one-piece intraocular lens according to claim 21, wherein the mixture comprising the hydrophilic monomer, the alkoxyalkyl methacrylate monomer, and the crosslinking monomer is polymerized in a tubular or cylindrical mold.

26. The method of forming a one-piece intraocular lens according to claim 21, wherein the mixture comprising the hydrophilic monomer, the alkoxyalkyl methacrylate monomer, and the crosslinking monomer is polymerized into a polymer rod comprising the copolymer.

27. The method of forming a one-piece intraocular lens according to claim 26, wherein the method further comprises forming a polymer blank or a polymer disc from the polymer rod and forming the intraocular lens from the polymer blank or the polymer disc.

\* \* \* \* \*